(12) United States Patent
Lafferty

(10) Patent No.: US 8,503,602 B2
(45) Date of Patent: *Aug. 6, 2013

(54) SYSTEM AND APPARATUS FOR RAPID STEREOTACTIC BREAST BIOPSY ANALYSIS

(76) Inventor: Peter R. Lafferty, New Albany, OH (US)

(*) Notice: Subject to any disclaimer, the term of this patent is extended or adjusted under 35 U.S.C. 154(b) by 504 days.

This patent is subject to a terminal disclaimer.

(21) Appl. No.: 12/754,005

(22) Filed: Apr. 5, 2010

(65) Prior Publication Data

US 2010/0191145 A1  Jul. 29, 2010

Related U.S. Application Data

(63) Continuation-in-part of application No. 11/863,684, filed on Sep. 28, 2007, now Pat. No. 7,715,523.

(60) Provisional application No. 60/827,327, filed on Sep. 28, 2006.

(51) Int. Cl.
*A61B 6/00* (2006.01)

(52) U.S. Cl.
USPC .............................................. 378/37

(58) Field of Classification Search
USPC .............. 378/65, 195, 196, 208, 37; 600/424, 600/429
See application file for complete search history.

(56) References Cited

U.S. PATENT DOCUMENTS

| 5,289,520 | A | * | 2/1994 | Pellegrino et al. | 378/37 |
| 5,383,234 | A | * | 1/1995 | Russell | 378/164 |
| 5,764,724 | A | * | 6/1998 | Ohlson | 378/167 |
| 7,715,523 | B2 | * | 5/2010 | Lafferty | 378/37 |

* cited by examiner

*Primary Examiner* — Glen Kao
(74) *Attorney, Agent, or Firm* — Standley Law Group LLP

(57) ABSTRACT

A stereotactic breast biopsy apparatus and system that may comprise an x-ray source, a digital imaging receptor, and a biopsy specimen cassette, wherein the digital imaging receptor is adjustably secured to the apparatus to permit an unobstructed illumination of the biopsy specimen and thereby produce biopsy x-ray images directly in the procedure room for immediate analysis. Some examples of the benefits may be, but are not limited to, a more rapid analysis of biopsy specimen digital images, post-processing image capability, and decreased procedure time and diminution of patient bleeding complications and needle discomfort.

7 Claims, 22 Drawing Sheets

SYSTEM AND APPARATUS FOR RAPID STEREOTACTIC BREAST BIOPSY ANALYSIS

This application is a continuation-in-part of and claims priority to U.S. application Ser. No. 11/863,684, filed Sep. 28, 2007, which claims priority to U.S. Provisional Application No. 60/827,327, filed Sep. 28, 2006, both of which are incorporated by reference as if fully recited herein.

TECHNICAL FIELD

Exemplary embodiments of the present invention relate to methods (e.g., medical non-surgical) of diagnosing breast cancer and, more particularly, to a novel apparatus, system, and method which beneficially improves current stereotactic breast biopsy devices and methods.

BACKGROUND OF THE ART

Stereotactic breast biopsy has become the method of choice for the non-surgical diagnosis of many forms of breast cancer. Many breast cancers are discovered by the presence of microcalcifications visible on a screening mammogram. Yet, these microcalcifications do not have a corresponding palpable abnormality. Therefore, an image-guided needle biopsy technique must be utilized to determine if early, pre-invasive breast cancer is present. Currently, stereotactically guided needle biopsy procedures represent the state-of-the-art for the common situation outlined above.

However, though very safe and minimally invasive, stereotactic breast biopsy can be laborious, time-consuming and uncomfortable for the patient. The procedure requires the patient to be prone. In order to immobilize the breast, physical compression must be applied to the breast during the procedure, and the patient must remain motionless. Procedure times are typically between 30-45 minutes, despite recent advances in vacuum-assisted biopsy needle technology. A significant component of procedure time continues to be consumed by the film development cycles required for specimen radiograph production.

A specimen radiograph is an ex-vivo x-ray picture of the biopsy samples or specimen "threads" retrieved from the breast. Under conventional circumstances, this radiograph must be performed outside the procedure room on a standard mammography x-ray unit. This picture is required to assure that sufficient quantities of microcalcifications are removed from the groups of calcium targeted within the breast. This process proves that the biopsy procedure will be adequate for subsequent analysis by surgical pathology. The process of performing specimen radiography is standard-of-care for stereotactic breast biopsy. Each specimen radiograph cycle can last 5-10 minutes, thereby adding 20-30% additional procedure time. If the original specimen radiograph demonstrates a paucity of microcalcifications, additional biopsy samples must be harvested, and the specimen radiograph cycle must be repeated.

SUMMARY OF THE INVENTION

One exemplary embodiment of the present invention is a modification and improvement to the commercially available stereotactic biopsy systems (e.g., LORAD Medical Systems Corp., Danbury, Conn. or Fischer Medical Technologies, Inc., Denver, Colo.). This modification may allow the stereotactic, swing-arm x-ray source (currently used solely to guide the biopsy procedure) to be used in the rapid production of specimen radiography. In one exemplary embodiment, a mechanical track may allow the x-ray source to shift laterally from the working biopsy corridor (occupied by the patient's breast during a procedure) allowing the x-ray source beam to be aligned with an add-on digital imaging receptor card which may be added to the lateral aspect of the existing imaging receptor. The harvested biopsy specimen threads may be positioned in, for example, specimen slots on a disposable specimen cassette or holder. The disposable specimen holder may then be attached to the add-on digital imaging receptor card between the x-ray source and digital imaging receptor card to allow for instant production of specimen radiographs within the procedure room. In another exemplary embodiment, an optional ancillary digital imaging receptor may be adjustably secured to at least a portion of the biopsy system to allow viewing of the harvested biopsy specimens without having to shift the axis of the x-ray source. Other exemplary embodiments are possible as set forth herein.

Some examples of the benefits may include, but are not limited to, the following:

a) Production of instant digital (rather than analog) specimen radiographs in the procedure room can be achieved. This feature can reduce procedure time up to 30%, thereby improving patient tolerance of the procedure.

b) Bleeding complications and needle discomfort can be diminished, as the typical number of samples harvested by the operator may decrease with exemplary embodiments of the present invention. There may no longer be a disincentive to "view" the biopsy sample early in the procedure, after a few samples have been retrieved.

c) The digital specimen radiograph can be "post-processed" (filtered and windowed) to assure adequate visualization of very small, subtle microcalcifications, (many of which may be less than 0.1 mm in diameter). This feature may improve the accuracy of stereotactic biopsy. With analog specimen radiography, these types of microcalcifications can be very difficult to reliably identify, resulting in the need for additional biopsy retrieval.

d) Decreased procedure time may allow for more procedures to be performed within a given time and level of staffing commitment. This may improve the economic viability of this procedure for biopsy centers.

These and other advantages may be provided by exemplary embodiments of the present invention, as described in more detail below.

BRIEF DESCRIPTION OF THE DRAWINGS

Other aspects of exemplary embodiments of the present invention will be readily apparent from the following descriptions of the drawings and exemplary embodiments.

DETAILED DESCRIPTION OF EXEMPLARY EMBODIMENT(S)

Figure 1:
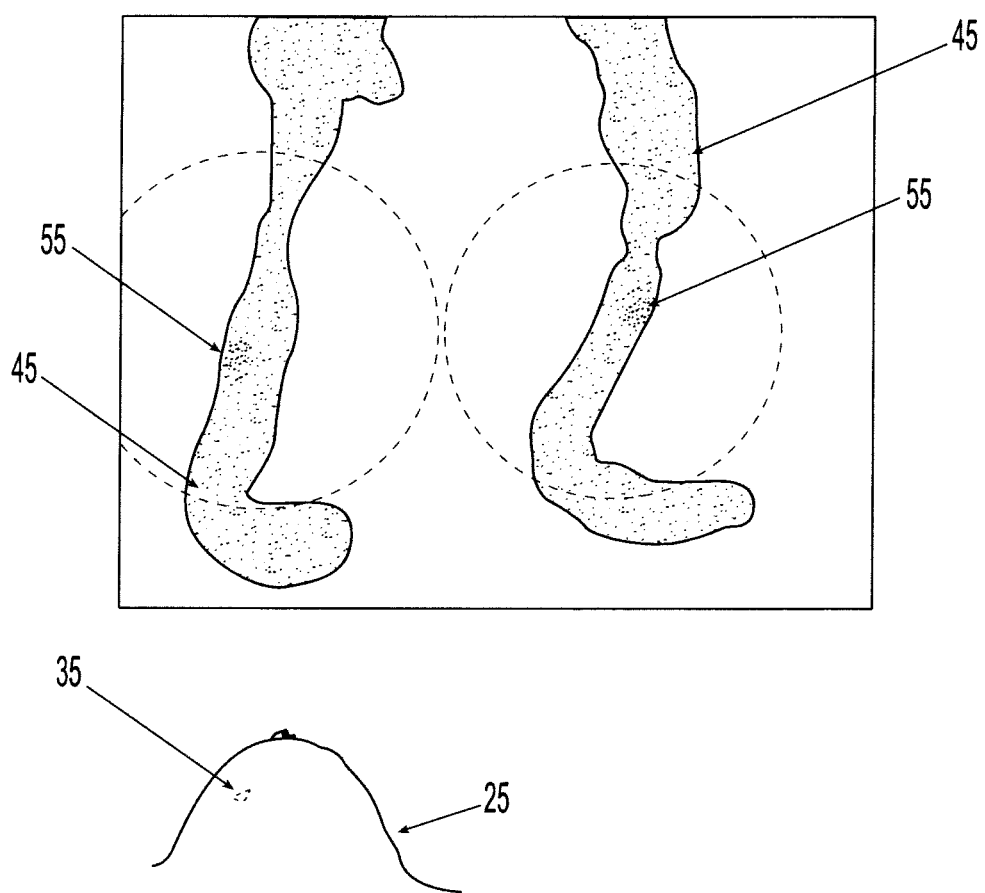
FIG. 1 illustrates an example of a breast biopsy specimen radiograph showing microcalcifications.

FIG. 1 illustrates a typical specimen radiograph showing a needle aspirated biopsy specimen 45 and microcalcifications 55. Biopsy specimens similar to 45 may be harvested from a patient's breast 25 typically via a plurality of samples collected from a target area 35. The specimen radiograph is an ex-vivo x-ray picture of the biopsy samples retrieved from the breast, which under conventional circumstances, must be processed outside the procedure room, on a standard mammography x-ray unit or on a separately purchased commercially available unit, such as one produced by Faxitron X-ray Corporation, Wheeling, Ill. In the current state of the art, this picture is required to assure that sufficient quantities of microcalcifications are removed from the groups of calcium targeted within the breast.

Figure 2:
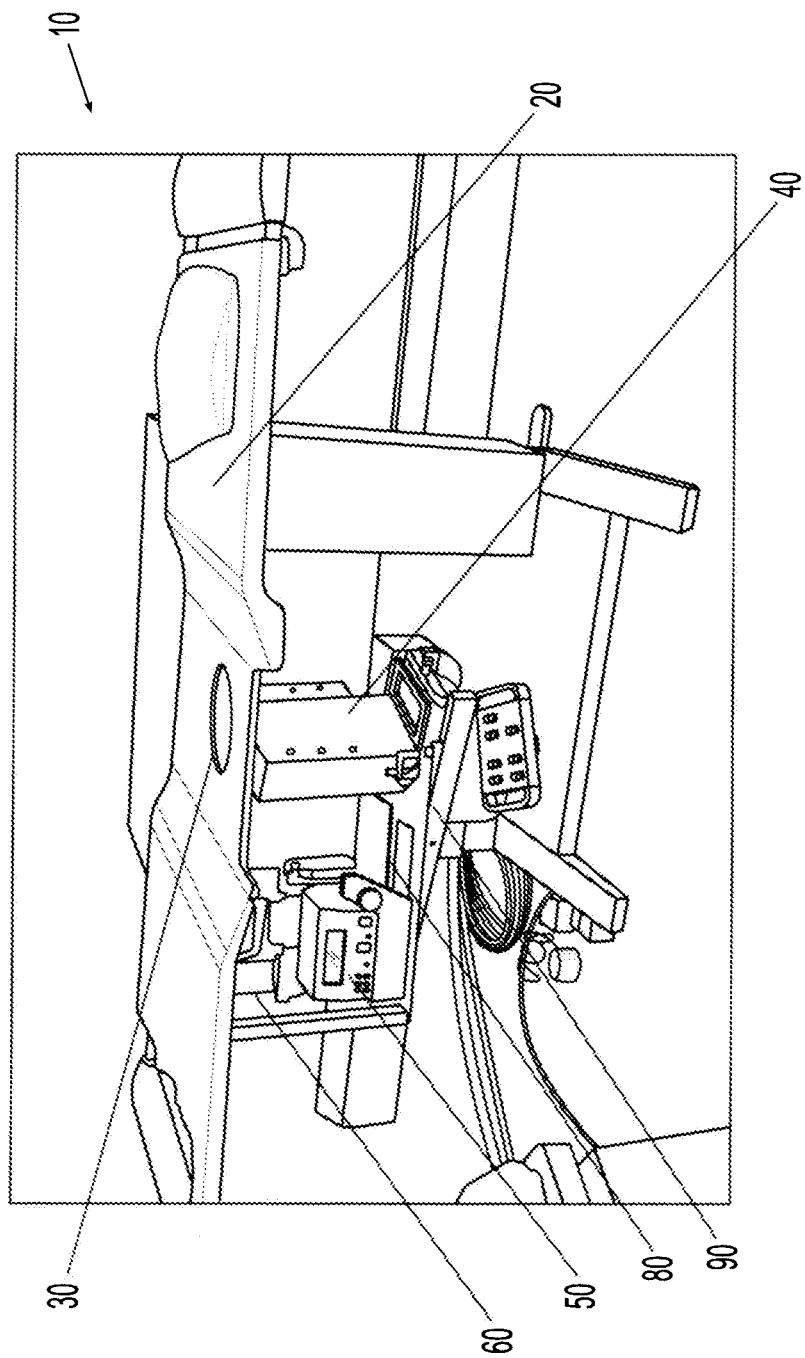
FIG. 2 illustrates a front perspective view of a typical stereotactic biopsy system (commercially available from LORAD).
Figure 3:
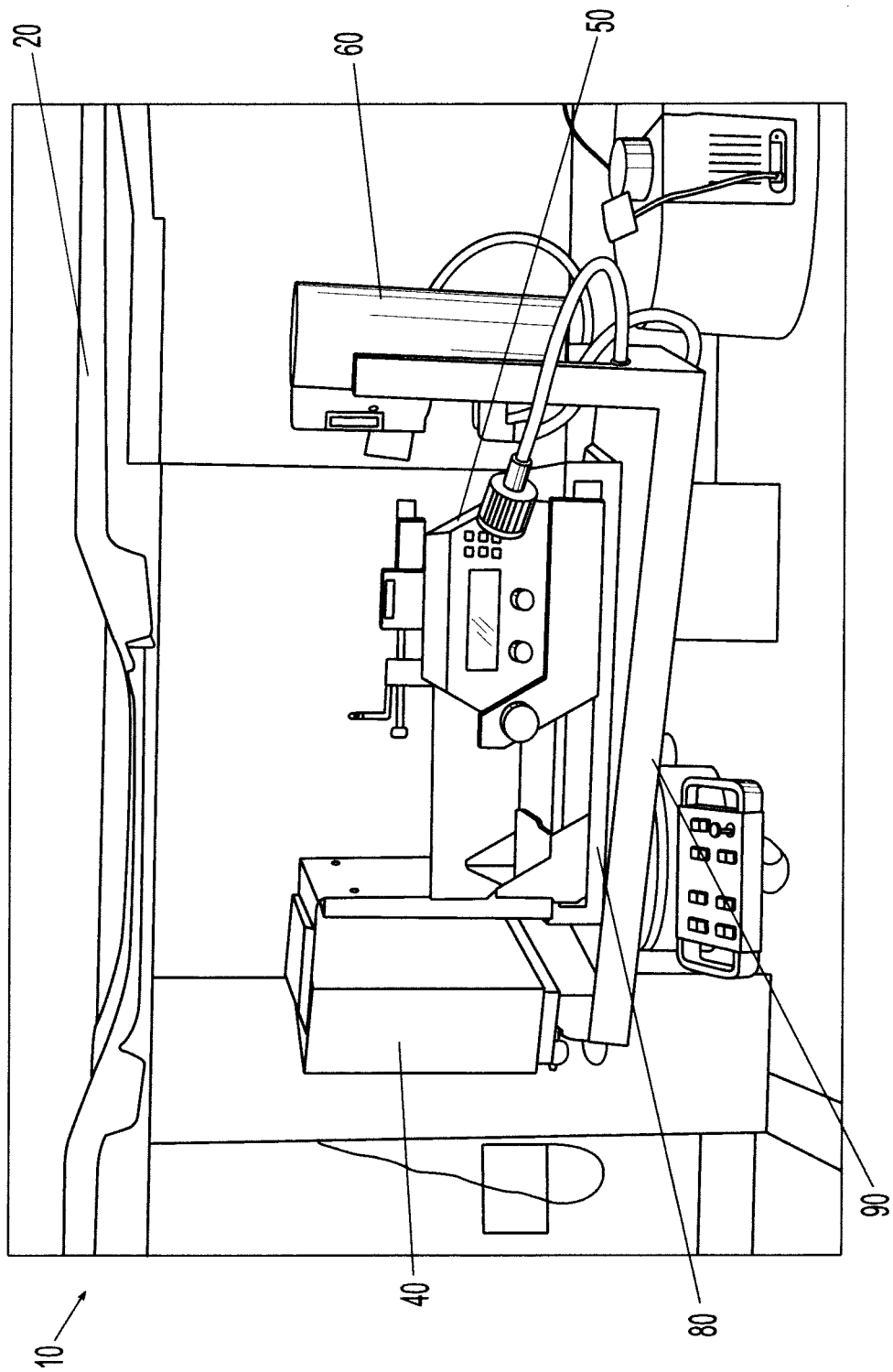
FIG. 3 illustrates a perspective view of a typical stereotactic biopsy system (commercially available from LORAD) showing details of the swing-arm x-ray source subassembly.
Figure 4:
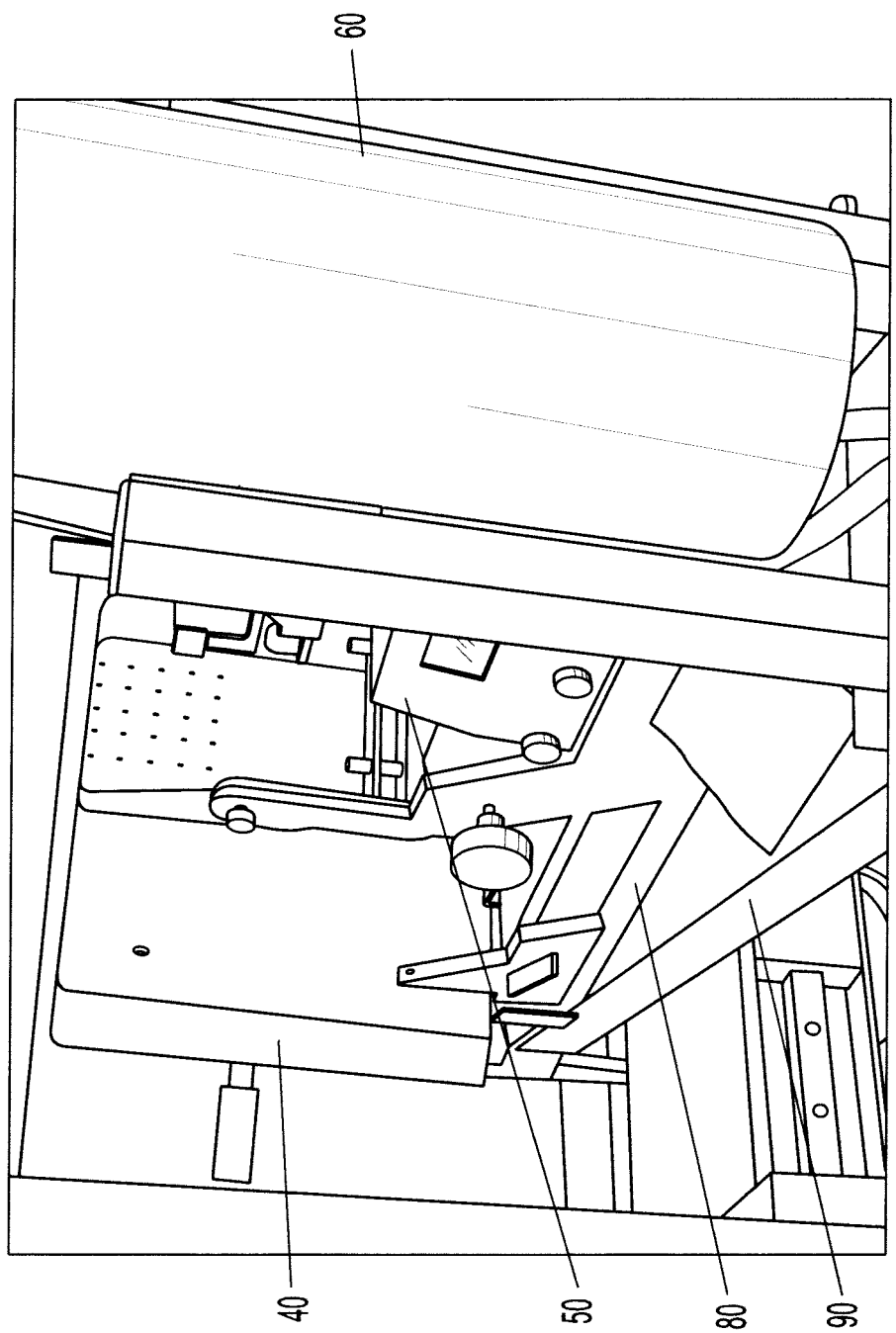
FIG. 4 illustrates a perspective view of a typical stereotactic biopsy system (commercially available from LORAD) showing details of the swing-arm x-ray source subassembly.

FIGS. 2, 3, and 4 illustrate a typical example of a commercially available stereotactic biopsy system 10 produced by LORAD Medical Systems Corp., Danbury, Conn. During a typical biopsy collection procedure, a patient is positioned in a prone position on table 20. The patient's breast under examination is allowed to protrude through a port 30 in table 20 and is captured and stabilized between a digital imaging receptor 40 and needle stage 50. The x-ray source 60 illuminates the breast with x-ray radiation forming an image on the digital imaging receptor 40, located on the distal side of the breast relative to x-ray source 60, for subsequent image processing. The collected x-ray image is reviewed and post-processed on a connected computer console and system in the procedure room. Foundation 80 and base 90 are rotatably connected which allows the physician to orient the x-ray source 60 and digital imaging receptor 40 to produce stereotactic image pairs that allow the physician to accurately position the tip of the biopsy needle (in x, y, and z coordinates) within the patient's breast.

Figure 5:
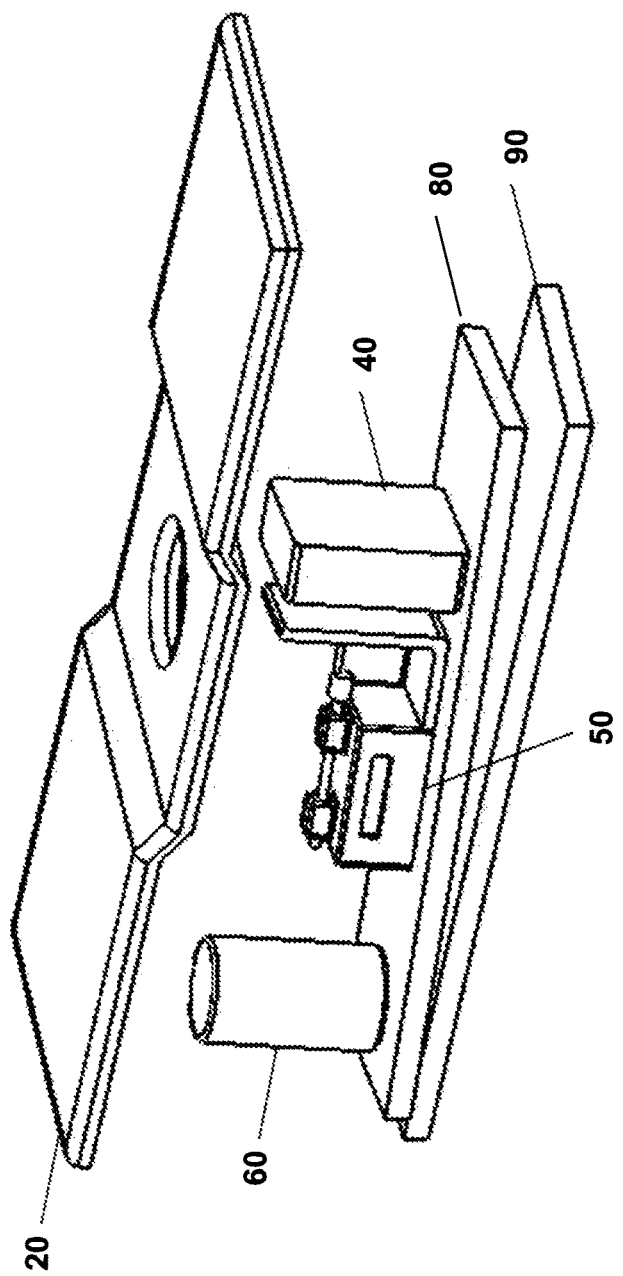
FIG. 5 illustrates a perspective schematic view of a typical stereotactic biopsy system showing exemplary components.
Figure 6:
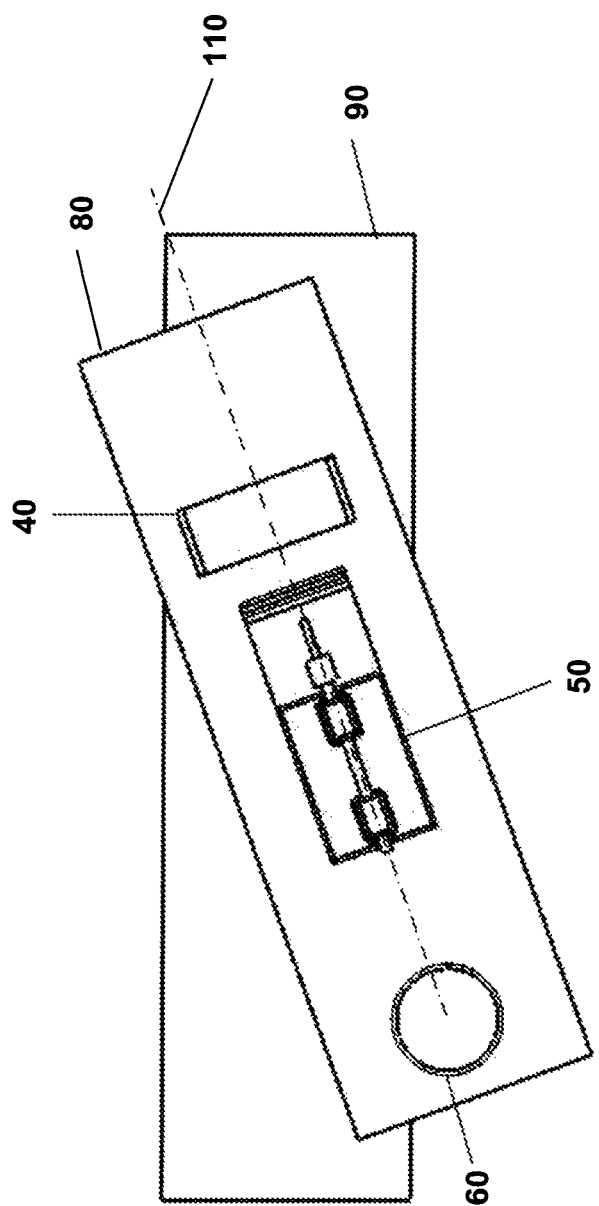
FIG. 6 illustrates a top plan schematic view of a typical stereotactic biopsy system showing exemplary components without a patient table.
Figure 7:
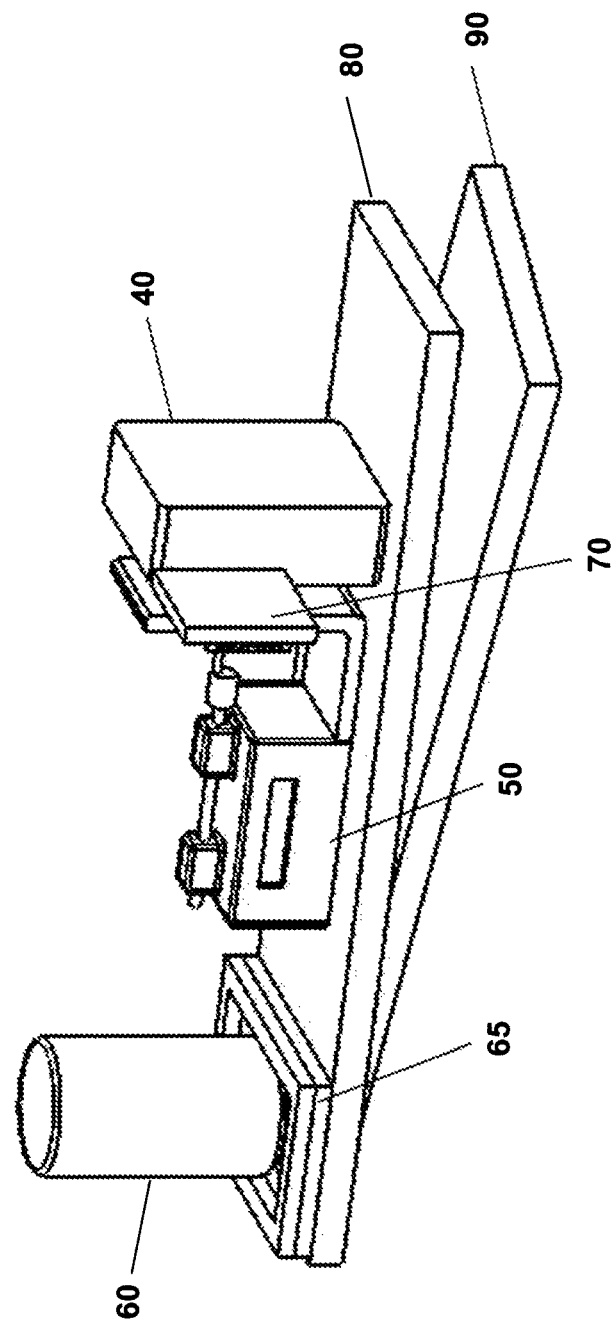
FIG. 7 illustrates a perspective schematic view of an exemplary embodiment of a stereotactic biopsy system of the present invention with the x-ray source in a stowed configuration.
Figure 8:
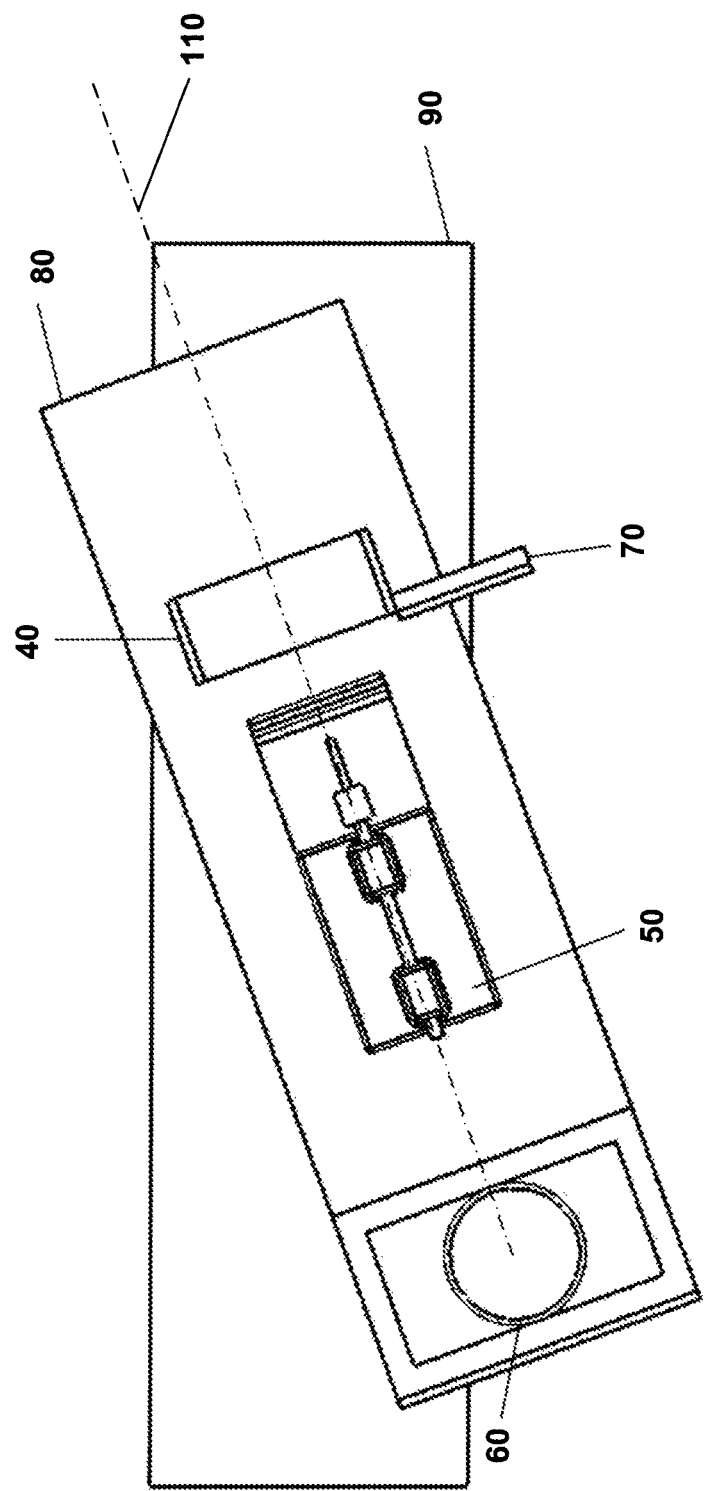
FIG. 8 illustrates a top plan schematic view of an exemplary embodiment of a stereotactic biopsy system of the present invention with the x-ray source in a stowed configuration.
Figure 9:
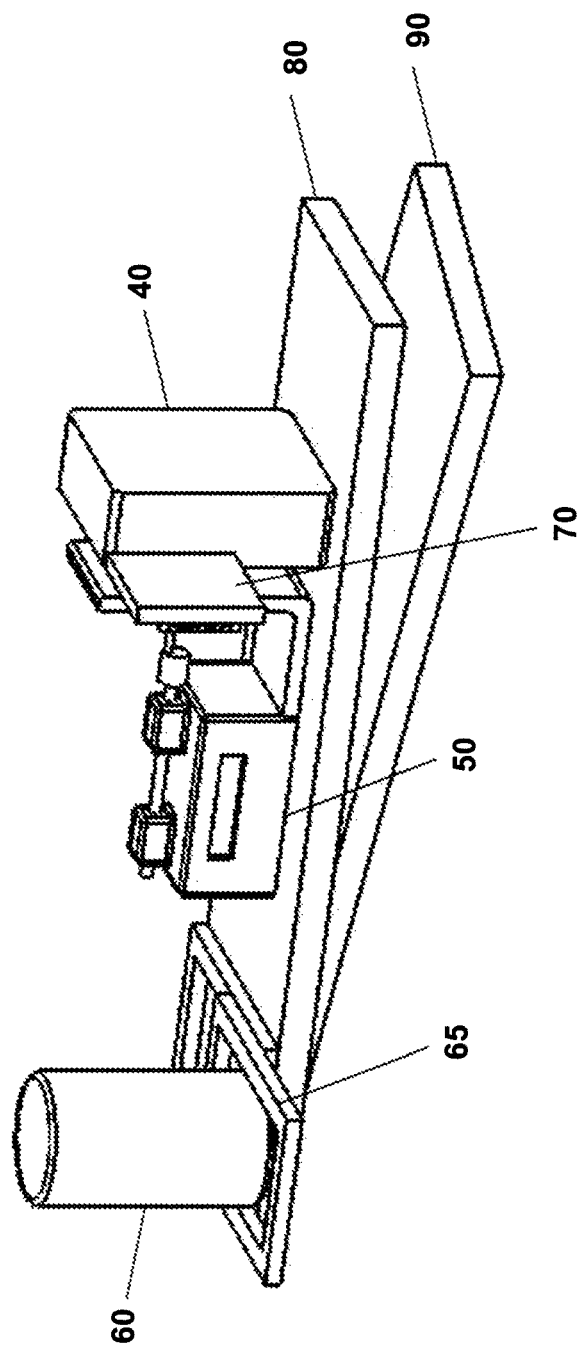
FIG. 9 illustrates a perspective schematic view of an exemplary embodiment of a stereotactic biopsy system of the present invention with the x-ray source in a deployed configuration.
Figure 10:
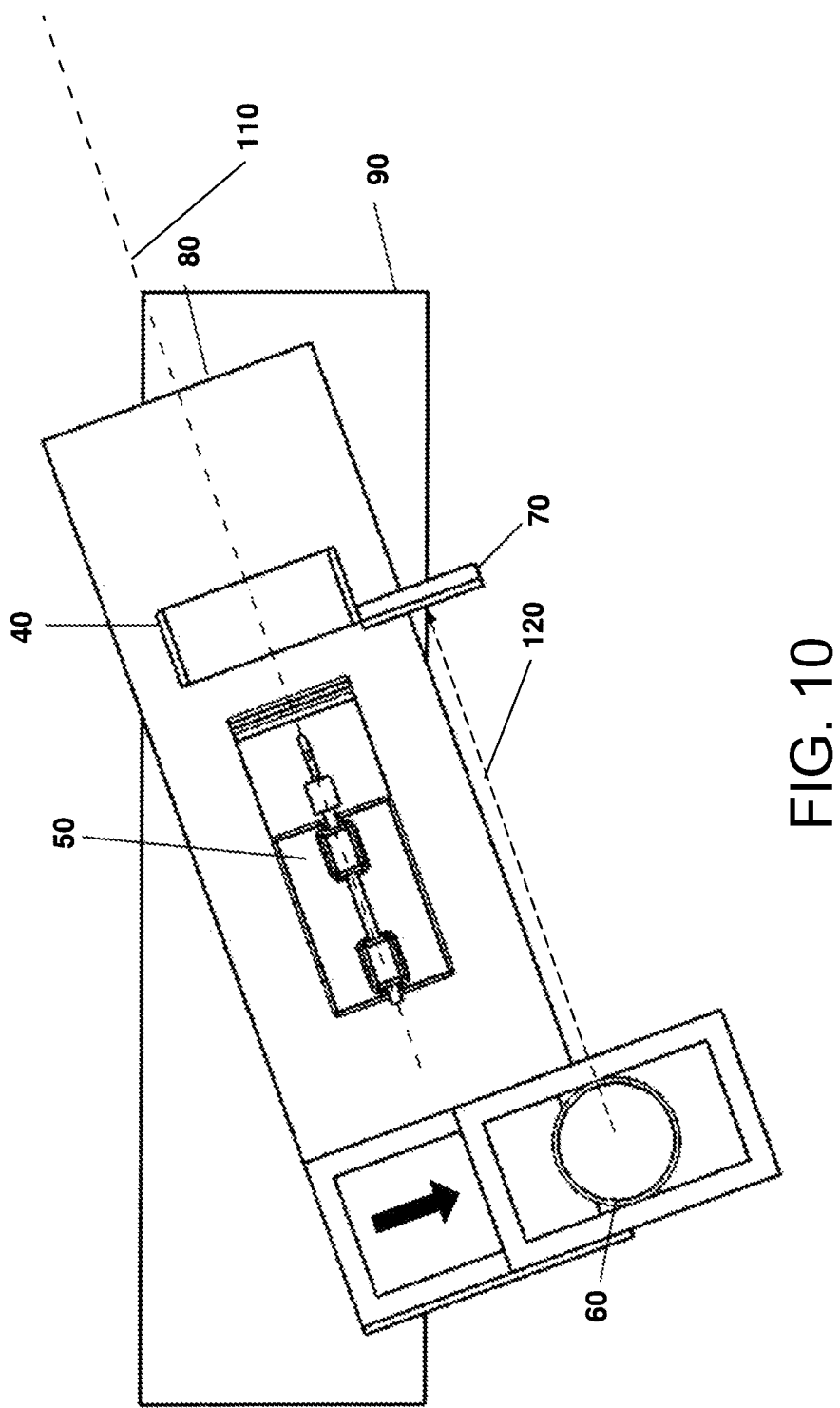
FIG. 10 illustrates a top plan schematic view of an exemplary embodiment of a stereotactic biopsy system of the present invention with the x-ray source in a deployed configuration.

Referring now to FIGS. 5 and 6, the x-ray source 60, which is fixedly attached to foundation 80, projects a radiation beam along a working biopsy corridor along beam axis 110 (occupied by the patient's breast during a procedure). During a typical biopsy harvesting procedure, a specimen radiograph is produced via an ex-vivo x-ray image of the biopsy samples retrieved from the breast. Under conventional circumstances, this radiograph must be performed outside the procedure room on a standard mammography x-ray unit or on a separately purchased Faxitron unit. This radiograph is required to assure that sufficient quantities of microcalcifications are removed from the groups of calcium targeted within the breast. This process proves that the biopsy procedure will be adequate for subsequent analysis by surgical pathology. Each specimen radiograph cycle can last 5-10 minutes, thereby adding 20-30% additional procedure time. If the original specimen radiograph demonstrates a paucity of microcalcifications, additional biopsy samples must be harvested and the specimen radiograph cycle must be repeated.

To provide quicker results, an exemplary embodiment of this invention may beneficially reduce the time needed to conduct the ex-vivo x-ray image processing steps described heretofore by allowing the physician to process and review x-ray images within a procedure room by means of modifications and improvements to, for example, commercially available stereotactic biopsy systems (e.g., LORAD, Fischer Medical Technologies, etc.). An example of this modification comprises a means by which the stereotactic, swing-arm x-ray source 60 (currently used solely to guide the biopsy procedure) may be, for example, displaced or rotated for use in concert with an imaging receptor to allow the rapid production of specimen radiography. In another example, the modification may include an add-on ancillary digital imaging receptor 70. In one example, the digital imaging receptor 70 may enage the underside face of the table 20.

FIGS. 7 through 11 illustrate an example of one exemplary embodiment of the present invention wherein a mechanical track system 65, which may be slidably attached to foundation 80 and support x-ray source 60, allows the x-ray source 60 to be laterally displaced from the working biopsy corridor along beam axis 110 (otherwise occupied by the patient's breast during a procedure). An add-on ancillary digital imaging receptor 70 is introduced and preferably positioned adjacent to digital imaging receptor 40, whereby the now displaced x-ray source beam 120 (shown in FIG. 10) may be aligned with a digital imaging receptor 70 to allow x-ray beam axis 120 to impinge normally upon the ancillary digital imaging receptor face 150, such as shown in the example of FIGS. 12 and 13.

A biopsy specimen retention device for retaining collected biopsy samples within the apparatus for analysis may be provided by a wide variety of mechanical support schemes. As shown as one example in FIGS. 11a, 11b, and 11c, harvested biopsy specimens 45 may be positioned in a specimen "cassette" 130 that may be fixedly or removably attached to an ancillary digital imaging receptor 70, which may be, in-turn, fixedly or removably associated with digital imaging receptor 40.

Figure 11A:
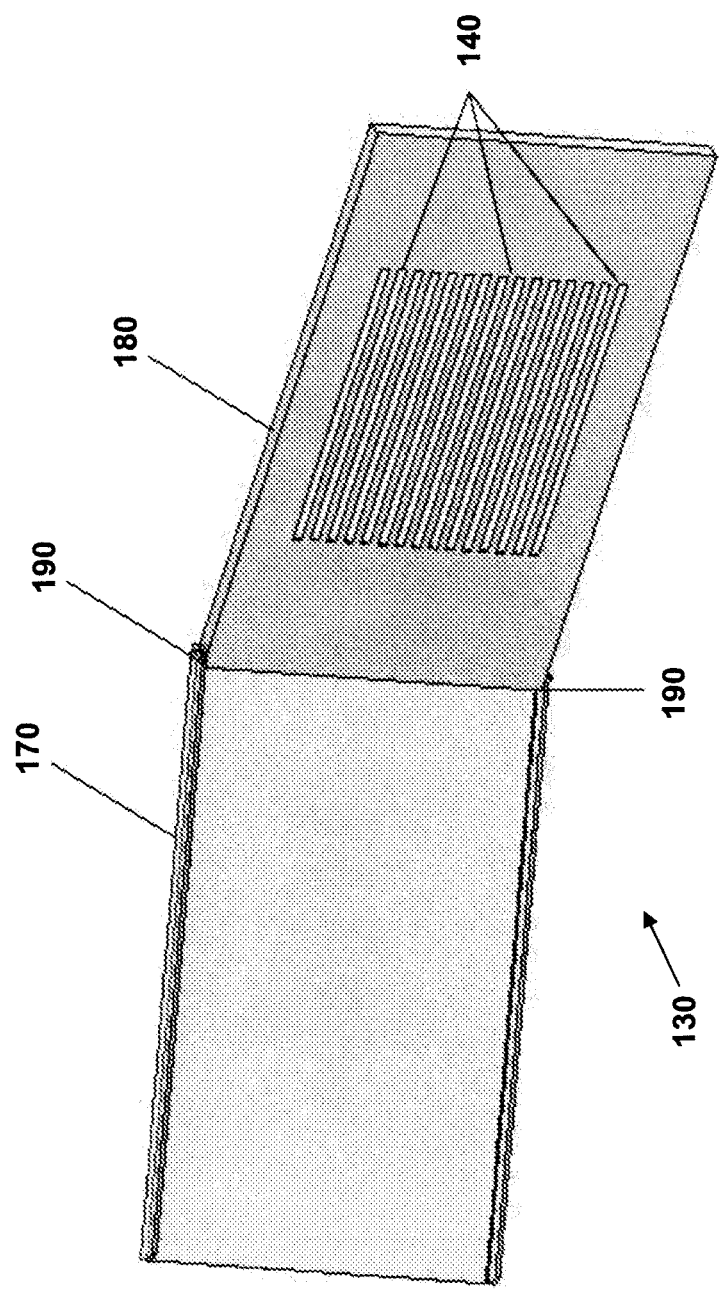
FIG. 11a illustrates a perspective schematic view showing one example of a specimen cassette with the specimen cover in an open position.
Figure 11B:
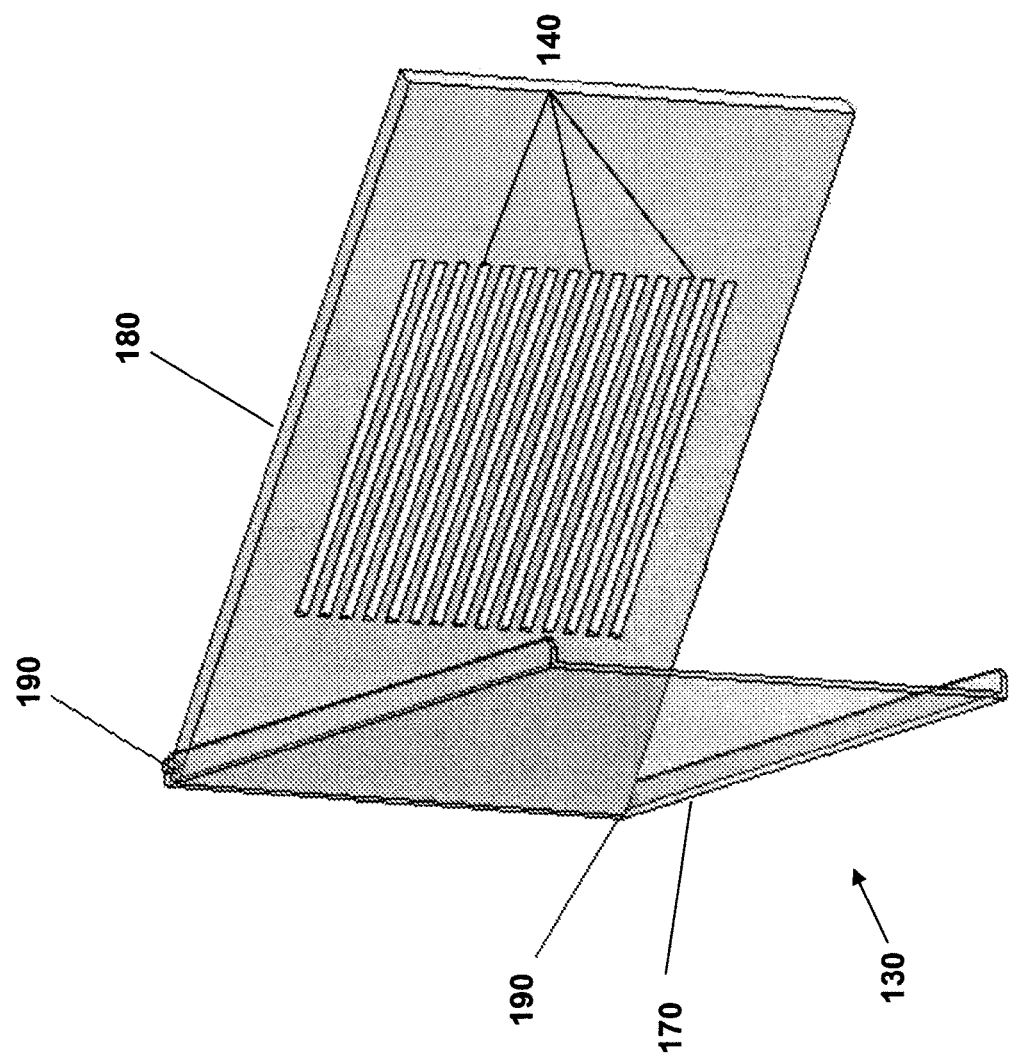
FIG. 11b illustrates a perspective schematic view showing one example of a specimen cassette with the specimen cover in a partially closed position.
Figure 11C:
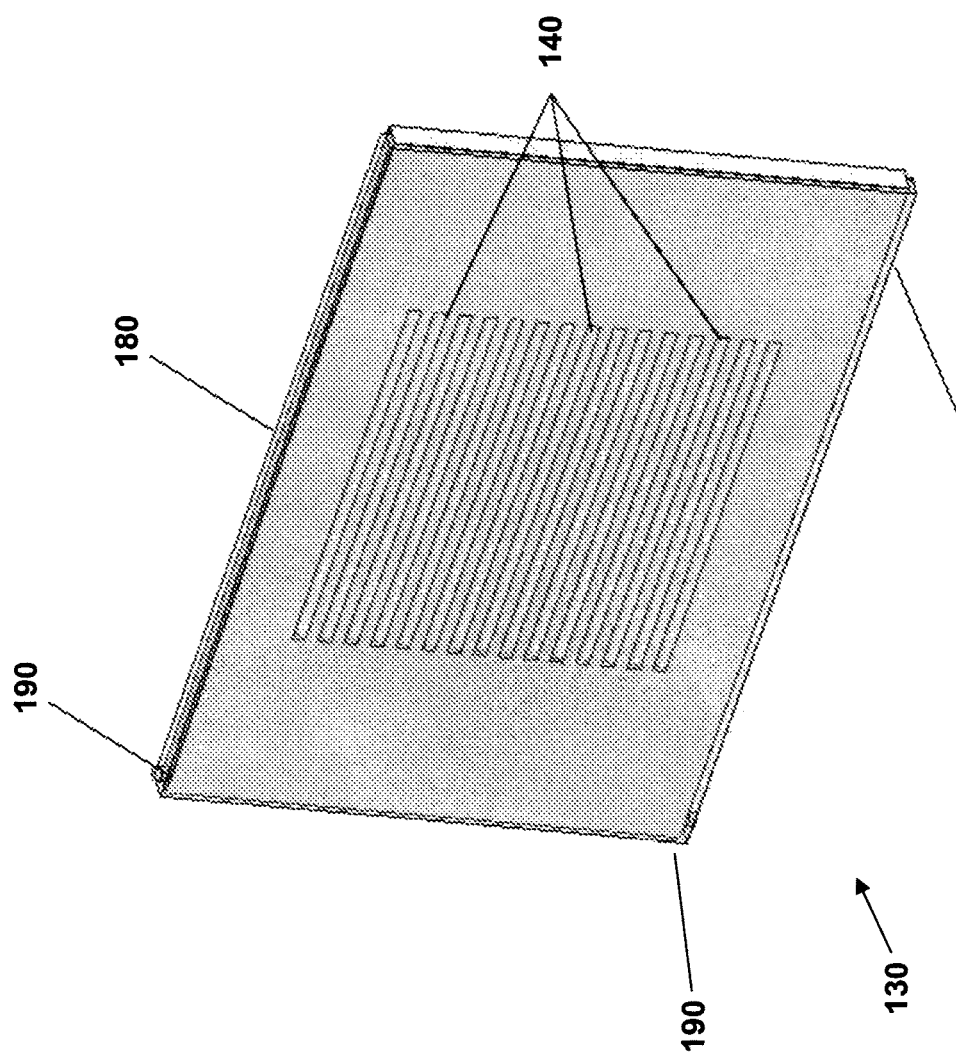
FIG. 11c illustrates a perspective schematic view showing one example of a specimen cassette with the specimen cover in a closed position.

In one exemplary embodiment, it may be preferable that the specimen cassette 130 be fabricated of x-ray transparent materials that are low in cost so as to promote disposability, such as paper-based materials or plastics, which may include, for example, polyethylene, polypropylene, polycarbonates, and polystyrenes, among others. FIG. 11a illustrates one example of a cassette 130 design which comprises a cassette base 180 that is hingedly attached to a cassette lid 170 via hinges 190. FIGS. 11b and 11c illustrate one example of a cassette lid 170 closure scheme. Other cassette base and cassette lid closure schemes are possible. For example, one exemplary embodiment may include the use of interlocking tongues and grooves on the cassette base 180 and cassette lid 170, which may allow for a slideable connection between cassette lid 170 and cassette base 180 instead of hinges 190. A single or plurality of specimen channels 140 may, for example, be formed as grooves within cassette base 180. Such specimen channels may provide cavities by which a single or plurality of biopsy specimens 45 may be captured within cassette 130 upon closure of cassette lid 170. The cassette 130 may allow biopsy specimens 45 to be positioned between the x-ray source 60 and ancillary digital imaging receptor 70 within beam 120, thereby allowing expeditious and direct biopsy image processing for instant production of specimen radiographs within the procedure room via a computer control monitor with consequent benefits heretofore described.

Figure 12:
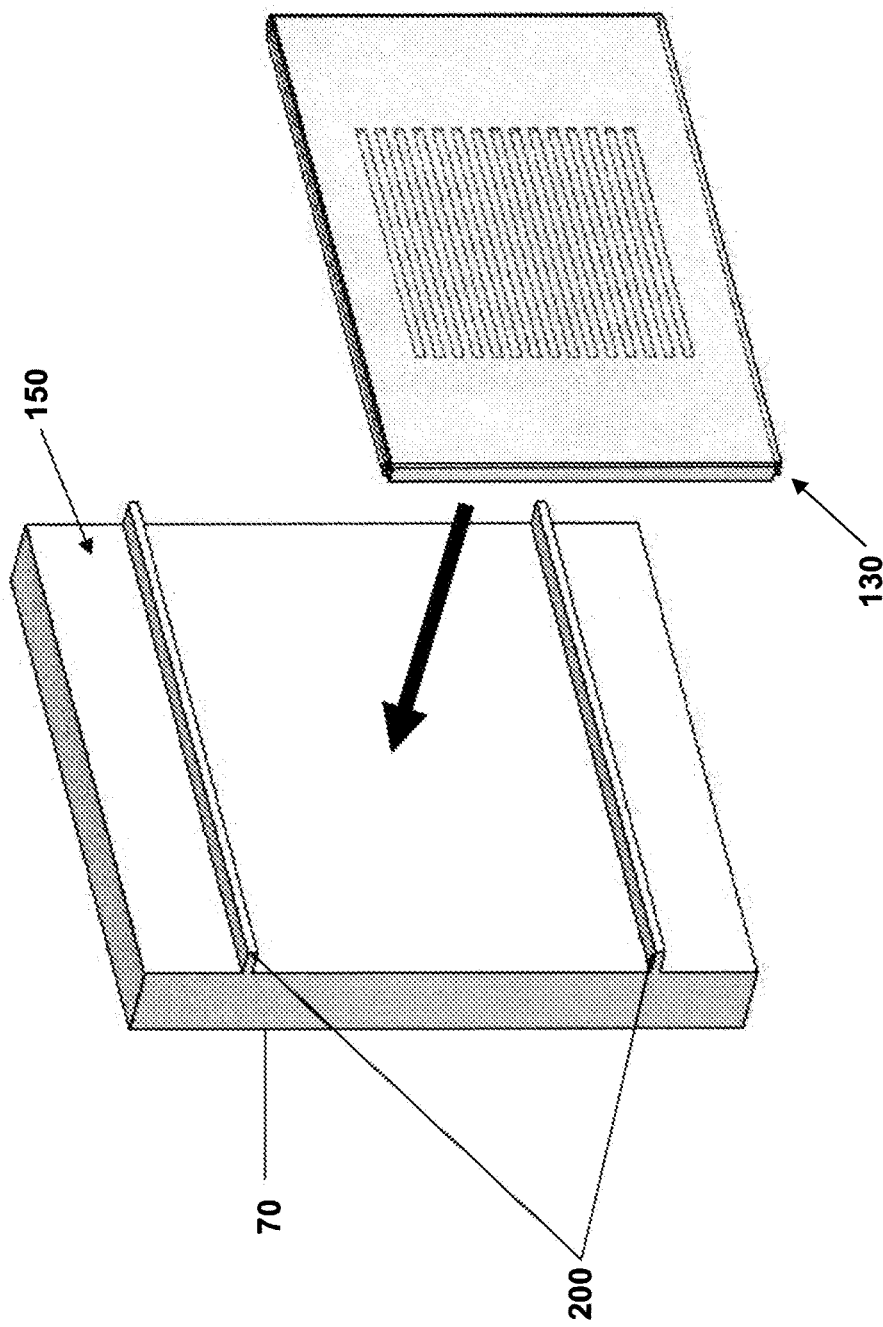
FIG. 12 illustrates a perspective exploded schematic view showing one example of a specimen cassette positioned for insertion onto a digital imaging receptor card.
Figure 13:
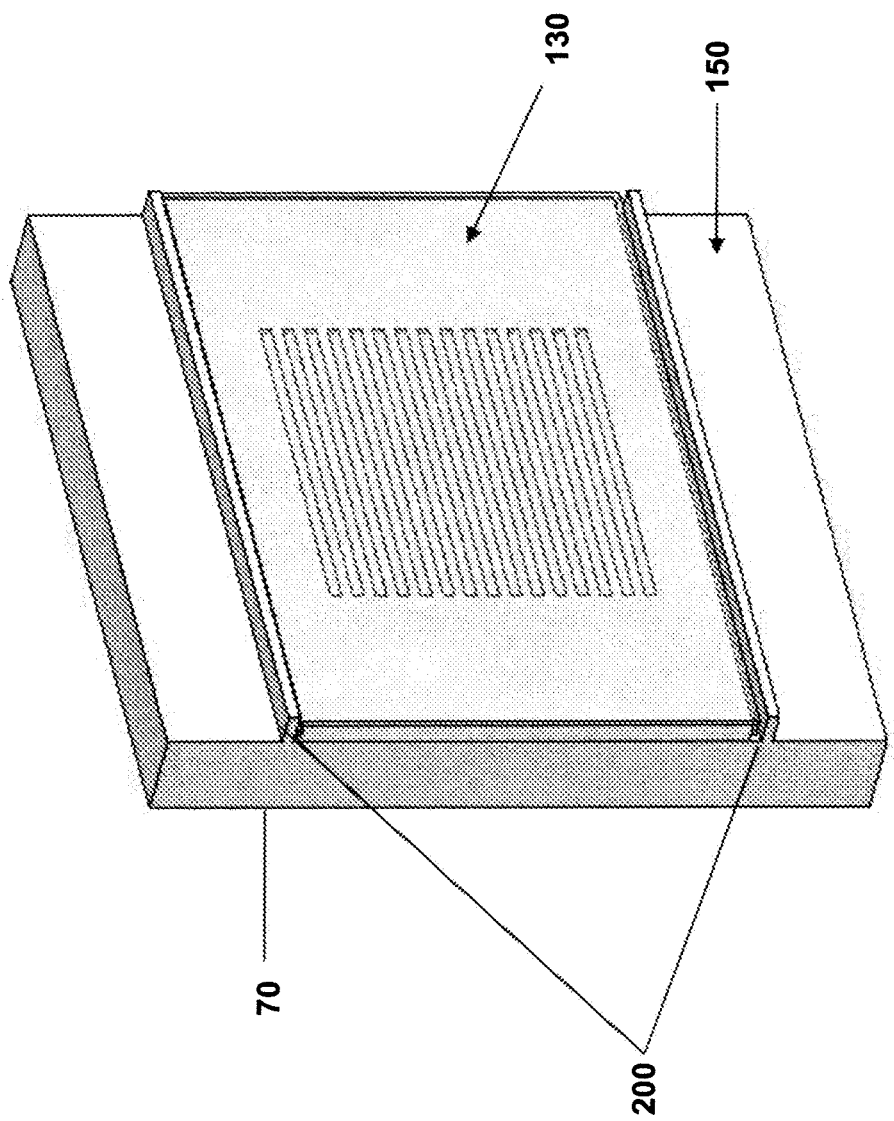
FIG. 13 illustrates a perspective schematic view showing one example of a specimen cassette positioned onto a digital imaging receptor card.

FIGS. 12 and 13 illustrate one example of one means by which cassette 130 may be removably attached to ancillary digital receptor 70. In this example, flanges 200 may be used to removably associate cassette 130 with ancillary digital imaging receptor face 150. Other means to removably associate cassette 130 with the ancillary digital imaging receptor face 150 may comprise, but are not limited to, hook and loop fasteners, contact adhesives, magnets, tongue and groove connections, mechanical fasteners, and other similar or suitable means.

Figure 14:
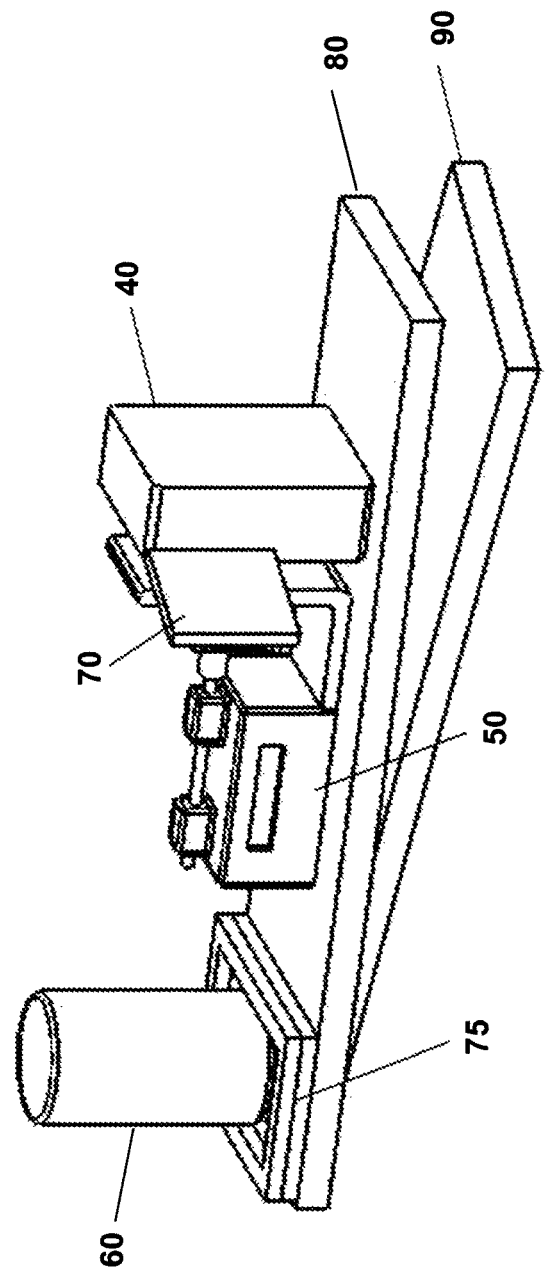
FIG. 14 illustrates a perspective schematic view of another exemplary embodiment of a stereotactic biopsy system of the present invention.
Figure 15:
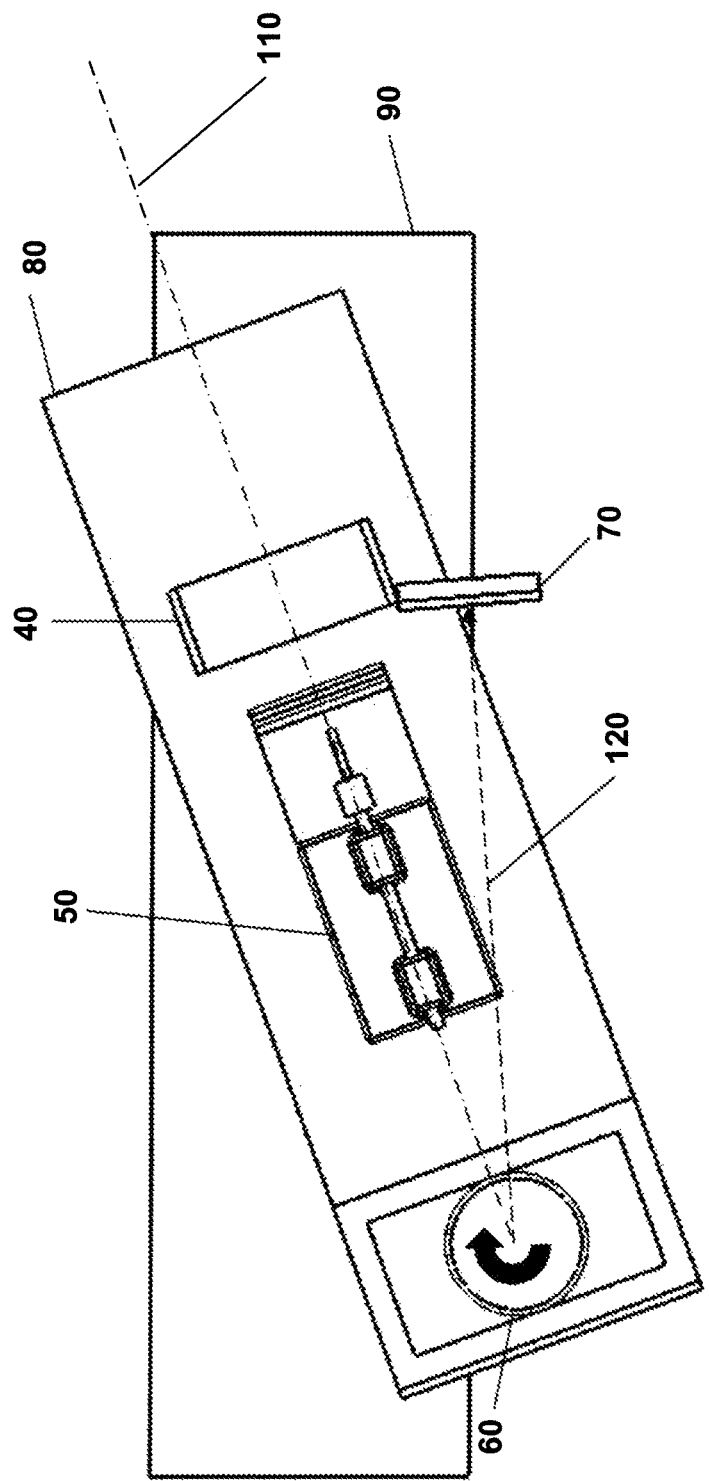
FIG. 15 illustrates a top plan schematic view of an exemplary embodiment of a stereotactic biopsy system of the present invention with the x-ray source in a rotated configuration.

FIGS. 14 and 15 illustrate an example of another exemplary embodiment wherein the x-ray source 60 is provided with a means to be rotatably connected about a longitudinal axis to foundation 80, whereby the x-ray source beam may be rotationally displaced from a working biopsy corridor beam axis 110 to position 120. In this example, ancillary digital imaging receptor 70 may be rigidly or adjustably associated with digital imaging receptor 40 or with a convenient point on foundation 80. Support means for x-ray source 60 may allow selective positioning of x-ray beam axis 120 so as to be normal to the ancillary digital imaging receptor face 150 shown in FIGS. 12 and 13 in this exemplary embodiment.

Other embodiments include, but are not limited to, means of rotationally and/or laterally displacing the x-ray source about or relative to any axis or axes to provide sufficient displacement of an x-ray source beam from a working biopsy corridor beam axis 110 to allow unobstructed x-ray source illumination of a collected biopsy specimen 45 contained within a specimen cassette 130 associated with an ancillary digital imaging receptor 70. It should be further noted that ancillary digital imaging receptor 70 may be fixedly or removably attached to a movable and adjustable support means (e.g., a cart, etc.) separate from (but in a suitable working vicinity of) a foundation 80 in some exemplary embodiments.

Figure 16:
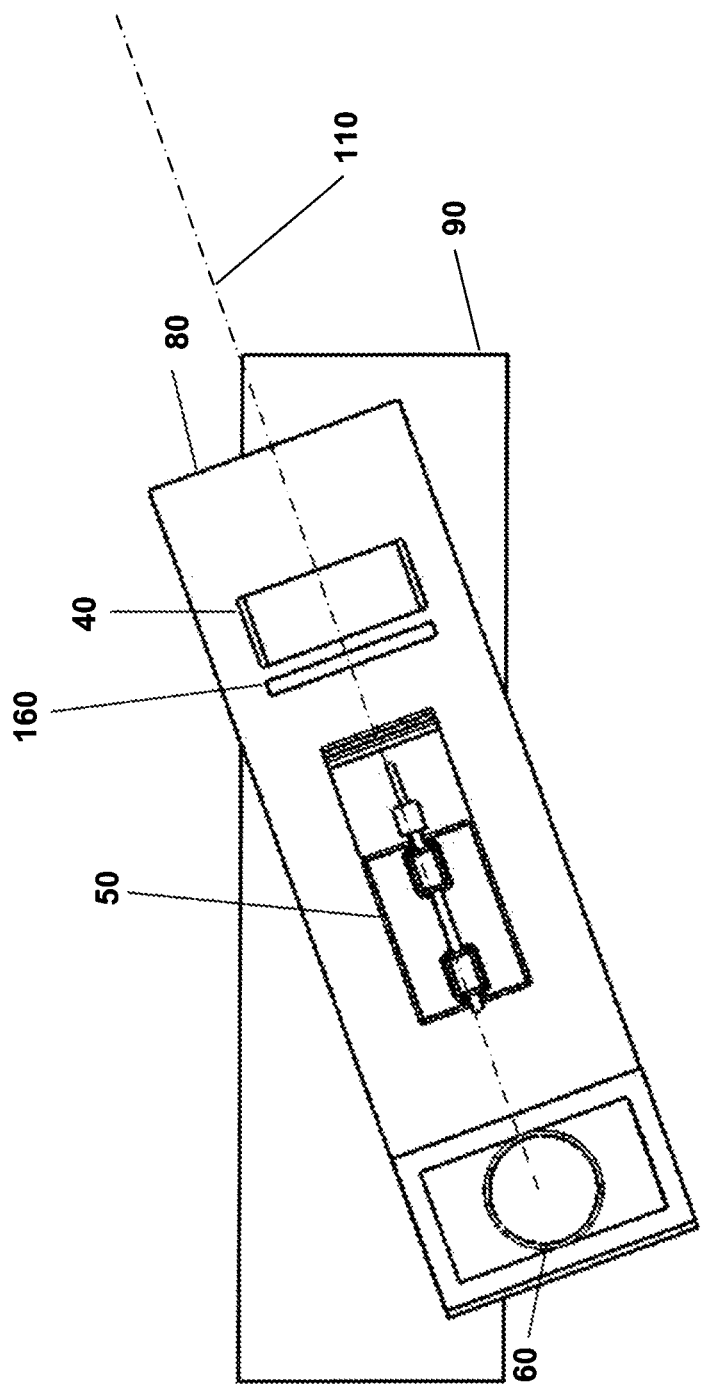
FIG. 16 illustrates a top plan schematic view of the present invention with an x-ray source and digital imaging receptor in respective stowed configurations.
Figure 17:
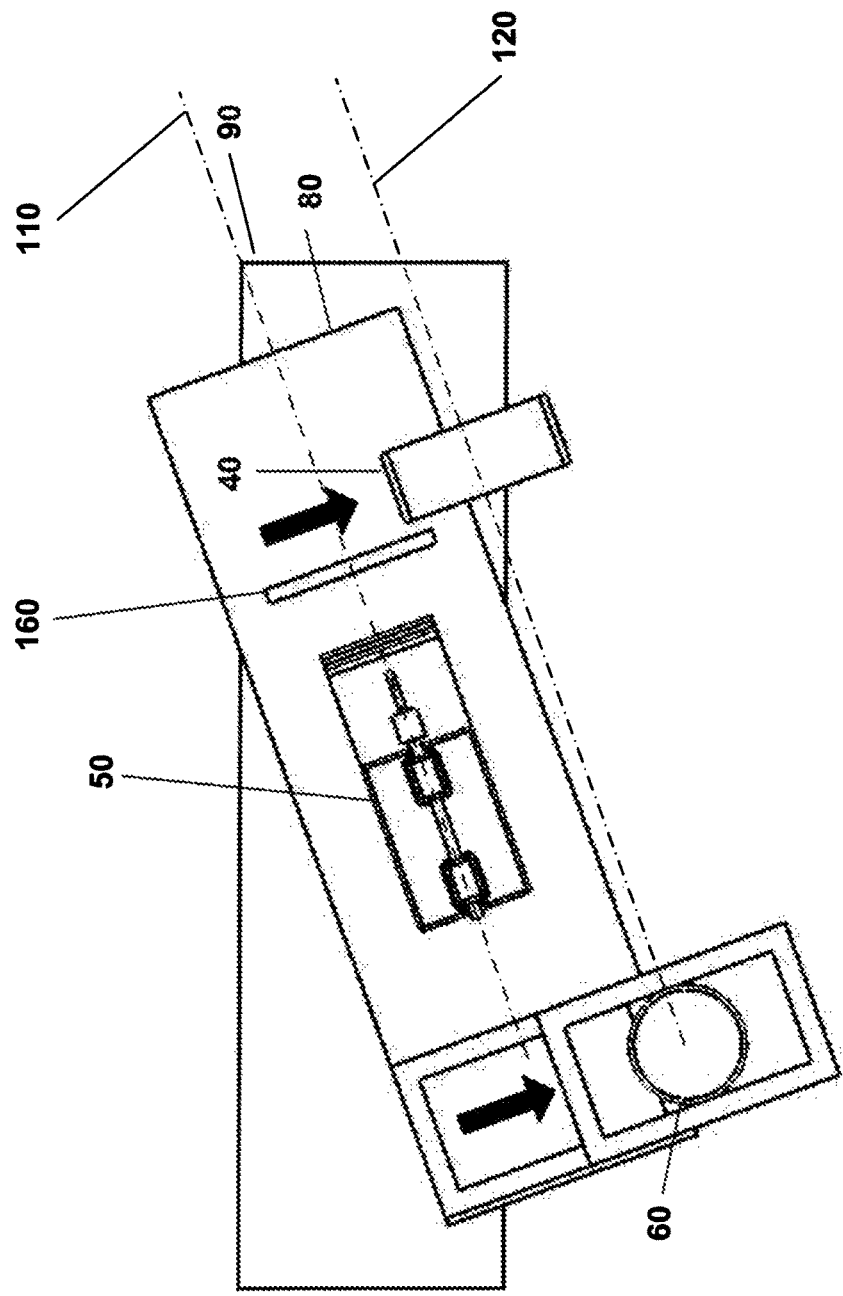
FIG. 17 illustrates a top plan schematic view of an exemplary embodiment of an x-ray source and digital imaging receptor in respective deployed configurations.

FIGS. 16 and 17 illustrate an additional embodiment, which includes a means for laterally and/or rotationally displacing an x-ray source 60, as heretofore taught, in concert with similar means for laterally and/or rotationally displacing a digital imaging receptor 40 to allow sufficient displacement of a radiation beam axis 120 from a working biopsy corridor 110, thereby allowing direct use of the digital imaging receptor 40 and eliminating the need for an ancillary digital imaging receptor 70. This latter embodiment may provide a means for capturing and stabilizing a breast by a breast support plate 160, which may be separately connected to foundation 80, allowing independent use and free movement of the digital imaging receptor 40. Furthermore, this exemplary embodiment may include a biopsy specimen cassette 130 that may be fixedly or removably associated with digital imaging receptor 40 in a manner similarly taught heretofore.

Figure 18:
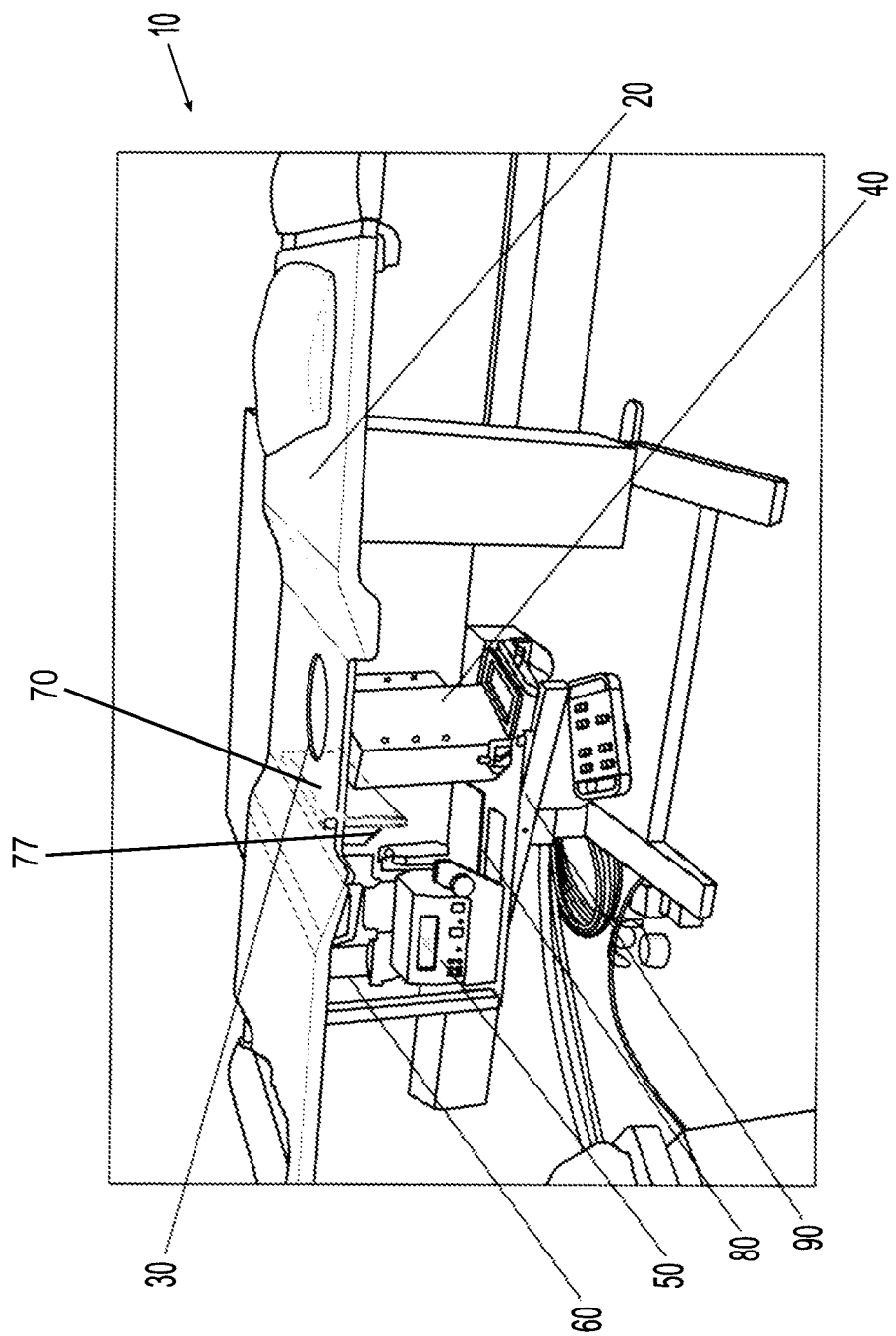
FIG. 18 illustrates a front perspective view of an exemplary stereotactic biopsy system with an exemplary embodiment of a digital imaging receptor attached thereto in an imaging position.
Figure 19:
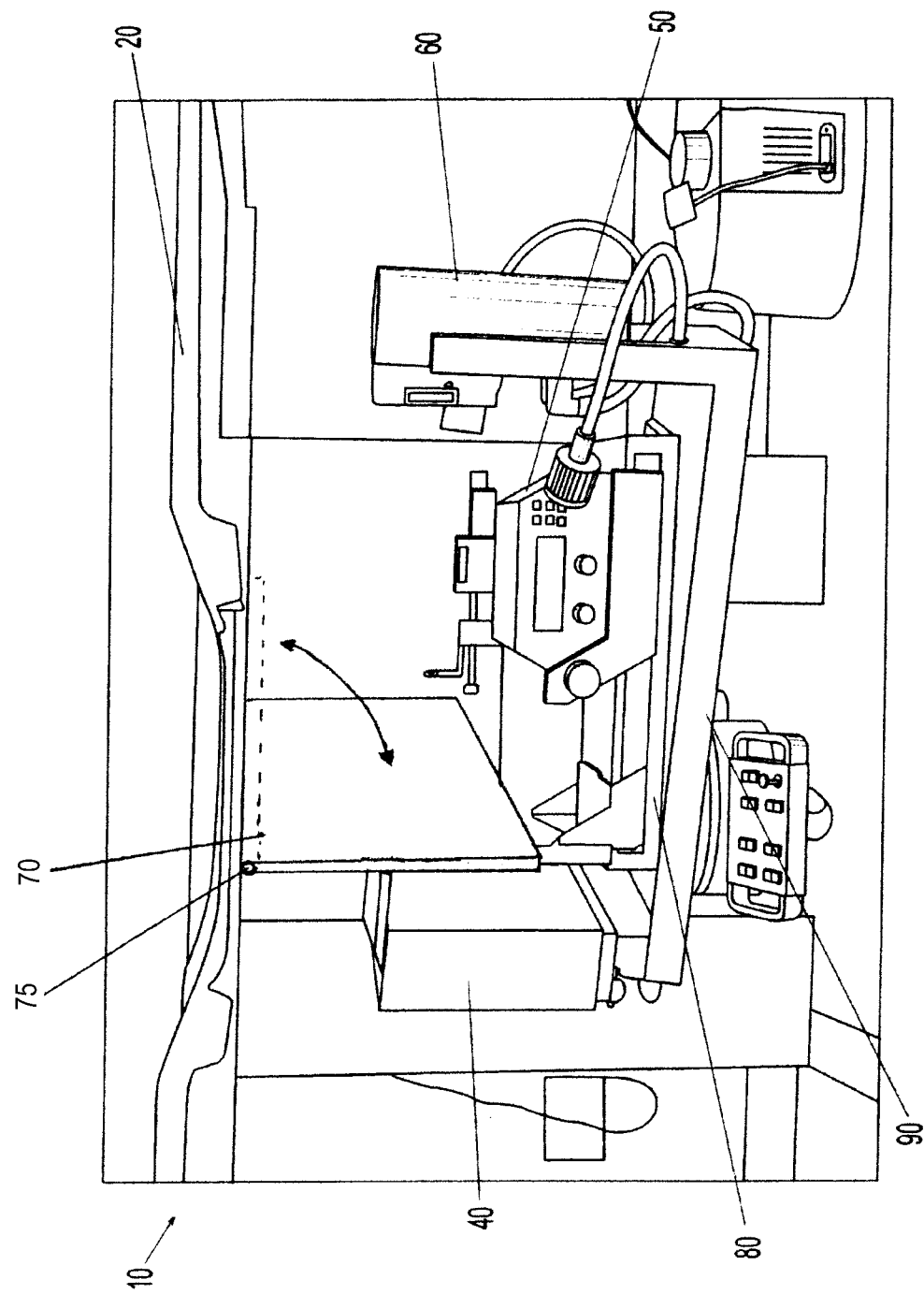
FIG. 19 illustrates a perspective view of an exemplary stereotactic biopsy system showing details of an exemplary swing-arm x-ray source subassembly, and depicting an exemplary method of movement of a digital imaging receptor attached thereto from an imaging position to a stored position.
Figure 20:
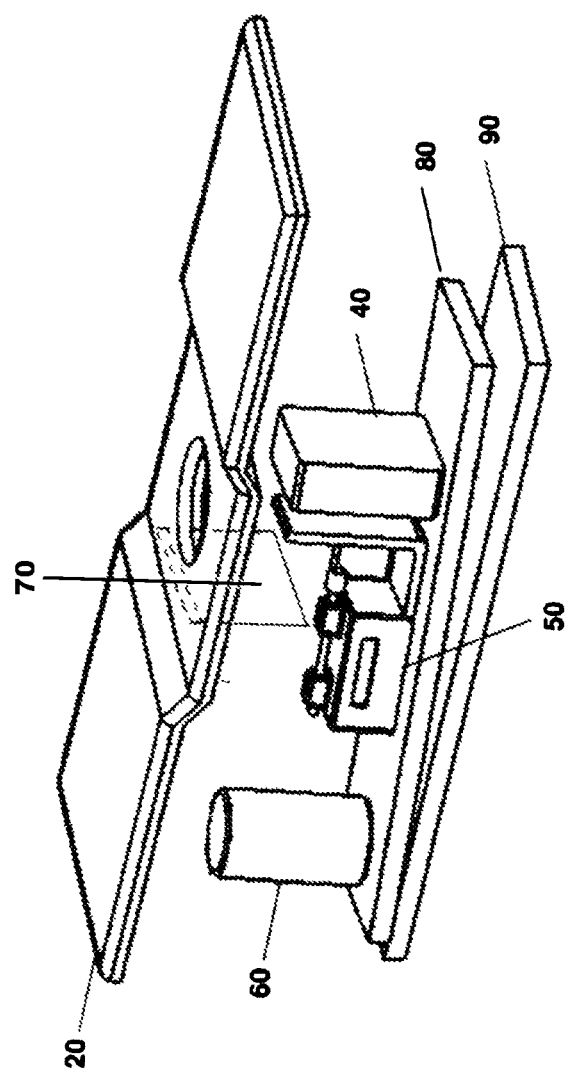
FIG. 20 illustrates a perspective view of an exemplary stereotactic biopsy system with an exemplary embodiment of a digital imaging receptor attached thereto in an imaging position.

In another example, as seen in FIGS. 18, 19, and 20, the ancillary digital imaging receptor 70 may be adjustably secured to at least a portion of the patient table 20. In exemplary embodiments, the ancillary digital imaging receptor 70 may be adapted to move between a stored position and an imaging position, such as depicted in the example of FIG. 19. The ancillary digital imaging receptor 70 may be adapted to move between the stored and imaging positions by rotation, pivoting, or other suitable forms or direction of movement.

When the system 10 is in use during the removal of a specimen, the ancillary digital imaging receptor 70 may be in a stored position out of the way of the procedure. In one example, such as depicted in FIG. 19, the ancillary imaging receptor 70 may be adjacent and substantially coplanar against the underside face of the patient table when in the stored position. In another example, the ancillary imaging receptor 70 may be positioned off to the side of the table 20 when in the stored position. In other examples, the ancillary imaging receptor 70 may be positioned in other suitable locations when in the stored position so as to allow for the removal of the biopsy specimen.

Likewise, when the system 10 is in use during the viewing of a specimen, the ancillary digital imaging receptor 70 may be in an imaging position such as shown in FIGS. 18-20 so as to be suitably aligned with the x-ray source. In one example, as depicted in FIG. 19, the ancillary imaging receptor 70 may be moved down and/or laterally to be positioned in the imaging position for viewing a specimen.

In one embodiment, the ancillary digital imaging receptor 70 may be adjustably secured by a pivotable attaching device 75, as seen in at least FIG. 19. However, other types of adjustable securing devices 75 may be used individually or in conjunction with each other, including, but not limited to: sliding tracks, swivel connections, pivotable connections, etc. In some examples, a device for adjustably securing the ancillary digital imaging receptor 70 may include one or more preset positions, such as the stored position and/or the imaging position, where the ancillary digital imaging receptor 70 may lock into place. The preset positions may facilitate the functioning of the ancillary digital imaging receptor 70 by aligning the receptor with the x-ray source 60.

Although an individual may move the digital imaging receptor 70 into position in some embodiments, in other embodiments the ancillary digital imaging receptor 70 may be automatically positioned by associating the receptor 70, or a portion thereof, with an automated positioning apparatus 77, such as depicted in FIG. 18. An automated apparatus 77 may employ any embodiment of a receptor 70, or alternatively, an automated apparatus 77 may employ just a portion of such an embodiment. For example, any of the receptors 70 shown and described herein may be attached to or associated with a robotic arm or other automated movement mechanism designed and/or programmed to effect receptor 70 positioning.

While certain exemplary embodiments of the present invention are described in detail above, the scope of the invention is not to be considered limited by such disclosure, and modifications are possible without departing from the spirit of the invention as evidenced by the following claims.

What is claimed is:

1. An apparatus adapted to be used for rapid stereotactic breast biopsy specimen analysis, said apparatus comprising:
    (a) an x-ray source;
    (b) a breast biopsy specimen cassette adapted to retain a breast biopsy specimen; and
    (c) a digital imaging receptor having a first side adapted to face said x-ray source and means for retention of said biopsy specimen cassette, said digital imaging receptor adapted to be positioned between a stored position and an imaging position;
    wherein said breast biopsy specimen cassette is adapted to be positioned between said x-ray source and said first side of said digital imaging receptor to permit x-ray images of said breast biopsy specimen to be formed upon said digital imaging receptor when subjected to x-ray illumination by said x-ray source, thereby facilitating rapid stereotactic breast biopsy analysis.

2. The apparatus of claim 1 wherein said digital imaging receptor is adjustably secured to at least a portion of a patient table associated with said apparatus.

3. The apparatus of claim 1 wherein said digital imaging receptor is adjustably secured to an underside face portion of a patient table associated with said apparatus.

4. The apparatus of claim 3 wherein the stored position is substantially coplanar with said patient table.

5. The apparatus of claim 3 wherein the imaging position is substantially perpendicular to said patient table.

6. The apparatus of claim 1 wherein said digital imaging receptor is ancillary to a second digital imaging receptor adapted to be used during collection of a breast biopsy specimen.

7. The apparatus of claim 1 further comprising a means for displacing an x-ray beam axis of said x-ray source from a first beam axis, wherein said means for displacing is associated with said x-ray source.

* * * * *